(12) United States Patent
Lee et al.

(10) Patent No.: US 10,203,294 B2
(45) Date of Patent: *Feb. 12, 2019

(54) INTERFACIAL CONCENTRATION AND ORIENTATION OF DROPLET CONTENTS FOR ENHANCED DETECTION USING ELECTRICAL IMPEDANCE SPECTROSCOPY

(71) Applicant: The Regents Of The University of California, Oakland, CA (US)

(72) Inventors: Abraham P Lee, Irvine, CA (US); Melinda G. Simon, Irvine, CA (US)

(73) Assignee: The Regents of The University of California, Oakland, CA (US)

(*) Notice: Subject to any disclaimer, the term of this patent is extended or adjusted under 35 U.S.C. 154(b) by 68 days.

This patent is subject to a terminal disclaimer.

(21) Appl. No.: 14/712,672

(22) Filed: May 14, 2015

(65) Prior Publication Data

US 2015/0330927 A1    Nov. 19, 2015

Related U.S. Application Data

(60) Provisional application No. 61/996,806, filed on May 14, 2014.

(51) Int. Cl.
| | |
|---|---|
| *G01N 33/553* | (2006.01) |
| *G01N 27/02* | (2006.01) |
| *G01N 33/487* | (2006.01) |
| *B01L 7/00* | (2006.01) |
| *C12Q 1/68* | (2018.01) |

(52) U.S. Cl.
CPC ............ *G01N 27/023* (2013.01); *B01L 7/52* (2013.01); *G01N 33/48721* (2013.01)

(58) Field of Classification Search
CPC ... B01L 7/52; G01N 27/023; G01N 33/48721
See application file for complete search history.

(56) References Cited

U.S. PATENT DOCUMENTS

| | | | |
|---|---|---|---|
| 2004/0234588 A1 | 11/2004 | Lu et al. | |
| 2005/0272096 A1 | 12/2005 | Clague et al. | |
| 2011/0086352 A1* | 4/2011 | Bashir | B01L 3/5027 435/6.11 |

(Continued)

OTHER PUBLICATIONS

Mazutis, L. et al., Lab on a Chip, vol. 9, pp. 2665-2672 (2009).*

(Continued)

*Primary Examiner* — Teresa E Strzelecka
(74) *Attorney, Agent, or Firm* — Nguyen & Tarbet Law Firm (57) ABSTRACT

System and method of concentrating (or aligning) analytes at a droplet-bulk solution interface as a means of enhancing a detection sensitivity of the analytes at electrodes in a fluidic channel. A number of differing types of intermolecular forces and chemicals or materials can be employed to accomplish the concentrating (and/or aligning). For example, a measurement analogous to a conventional electrical impedance spectroscopy (EIS) measurement can be made by bringing an analyte (e.g., a molecule to be detected) to the edge of a droplet, and in so doing, positioning the analyte close to an electrode surface to aid in detection.

7 Claims, 5 Drawing Sheets

(56) References Cited

U.S. PATENT DOCUMENTS

2012/0034155 A1  2/2012 Hyde et al.
2013/0154671 A1  6/2013 Lee et al.

OTHER PUBLICATIONS

Simon, M.G. et al., Label-Free Detection of DNA Amplification in Dropletsusing Electrical Impedance, 15th International Conference on Miniaturized Systems for Chemistry and Life Sciences 2011 (MicroTAS 2011), pp. 1683-1685 (Year: 2011).*

* cited by examiner

INTERFACIAL CONCENTRATION AND ORIENTATION OF DROPLET CONTENTS FOR ENHANCED DETECTION USING ELECTRICAL IMPEDANCE SPECTROSCOPY

CROSS-REFERENCE TO RELATED APPLICATIONS

This application claims the benefit of U.S. Provisional Application No. 61/996,806, entitled INTERFACIAL CONCENTRATION AND ORIENTATION OF DROPLET CONTENTS FOR ENHANCED DETECTION USING ELECTRICAL IMPEDANCE SPECTROSCOPY, filed May 14, 2014, the benefit of the earlier filing date of which is hereby claimed under 35 U.S.C. § 119(e) and the contents of which are further incorporated by reference in their entirety.

FIELD OF THE INVENTION

Embodiments of the present invention generally relate to molecular body detection. More specifically, embodiments of the present invention relate to detection of analyte bodies contained within a droplet.

BACKGROUND

Detection of DNA amplification in droplets after polymerase chain reaction (PCR) has been demonstrated, mainly by use of fluorescent labels (e.g., probes, such as the Taqman probe) as markers for amplification events. As DNA is amplified, a fluorophore is released from its quenching molecule, and fluorescence can result when the sample is interrogated with an appropriate wavelength of light.

Despite the widespread use of this technique, there are several disadvantages to detecting reaction events via fluorescence, including the need for a fluorescent microscope and expensive optical equipment, the extra processing steps and expense required to incorporate fluorophore and quencher molecules into a probe, and the qualitative or inconsistent result that fluorescence measurements provide (e.g., as a result of photobleaching effects). In particular, photobleaching possesses the drawback of requiring normalization of fluorescent signals in order to quantify results. Alternative techniques for detection of nucleic acid amplification events include staining with an intercalating dye, such as ethidium bromide or SYBR Green. However, these materials are hazardous to work with and bind non-specifically to all double-stranded DNA.

Prior approaches using the concept of electrical impedance spectroscopy (EIS) have achieved high-sensitivity detection of nucleic acids and proteins by measuring direct binding events of molecules to the surface of an electrode. To induce binding, the electrode surface can be functionalized with a variety of materials, such as complementary nucleic acid strands, antibodies, or antigen molecules. Binding of a sufficient number of molecules of interest to the electrode surface is detectable as a change in the impedance of the system. However, conventional systems require static measurement, wherein molecules must be conjugated directly to the electrode surface. This is an inherently slow process, and one that is not amenable to high-throughput or continuous processing. Detection of binding events typically requires timescales on the order of tens of minutes. Further, multiplexed detection using fluorescence is limited by the number of available fluorescent probes, which is governed by the physical phenomenon of spectral overlap of these probes.

SUMMARY

In one aspect a system and method of concentrating (or aligning) analytes at a droplet-bulk solution interface as a means of enhancing a detection sensitivity of the analytes at electrodes in a fluidic channel is disclosed. A number of differing types of intermolecular forces and chemicals or materials can be employed to accomplish the concentrating (and/or aligning). For example, a measurement analogous to a conventional electrical impedance spectroscopy (EIS) measurement can be made by bringing an analyte (e.g., a molecule to be detected) to the edge of a droplet, and in so doing, positioning the analyte close to an electrode surface to aid in detection.

In one embodiment a method of determining a composition of molecules in a droplet includes providing a set of detection electrodes in contact with a fluidic channel, concentrating an analyte at an interfacial boundary of a droplet, providing the droplet in vicinity of the set of detection electrodes through the fluidic channel, applying an alternating current (AC) power at a first frequency across the set of detection electrodes, obtaining a first measurement value reflecting electrical impedance of the droplet at the first frequency, comparing the first measurement value reflecting electrical impedance of the droplet with a first corresponding reference value, wherein the first corresponding reference value is obtained by measuring a reference droplet containing a known analyte amount in suspension within the reference droplet at the first frequency, and determining presence of analyte in suspension within the droplet based on the comparison.

In an embodiment, the concentrating includes the association of a cationic surfactant with the droplet periphery. In a further embodiment, the cationic surfactant includes hexadecyltrimethylammonium bromide (CTAB). In an embodiment, the analyte includes one of a nucleic acid monomer and a protein. In an embodiment, the set of detection electrodes includes at least two planar electrodes. In a further embodiment, peak or peak-to-peak voltages are derived from respective real time voltage-time plots produced by an impedance scope in combination with a current amplifier. In a further embodiment, the set of detection electrodes includes two groups of electrodes, wherein the two groups share a common excitation or detection electrode, and obtaining the first measurement value further includes a differential impedance measurement conducted across the two groups of detection electrodes respectively. In a further embodiment the method includes performing at least three additional differential impedance measurements on the droplet at three additional frequencies conducted across the set of detection electrodes, comparing peak-to-peak voltage values obtained from the three additional measurements with three corresponding reference values respectively, wherein the three corresponding reference values are obtained by measuring the reference droplet at the three additional frequencies respectively, and determining presence of analyte in suspension within the droplet by incorporating results from the three additional measurements. In an embodiment, the test droplet is in motion relative to the set of detection electrodes while obtaining the first measurement value.

In an embodiment a system for detecting presence of an analyte in a droplet includes a fluidic channel providing a droplet, a surfactant operable for concentrating an analyte at an interfacial boundary of the droplet, a set of detection electrodes disposed in contact with the fluidic channel, an AC power supply operable to apply electrical powers across the set of detection electrodes at a plurality of known frequencies, an impedance measurement device operable to measure electrical impedance of the droplet, and a processor operable to compare measured electrical impedance of the droplet with corresponding reference electrical impedances and to determine presence of analyte in suspension within the droplet based on comparison, wherein the corresponding reference electrical impedances are obtained by measuring a reference droplet at the plurality of known frequencies respectively, and wherein the corresponding reference droplet contains known amount of analyte in suspension within the reference droplet.

In an embodiment the system includes a thermocycling region for implementing PCR in the droplet. In an embodiment the analyte includes one of amplified nucleic acid, non-amplified nucleic acid, and protein. In an embodiment the impedance measurement device is operable to measure the droplet in motion relative to the set of detection electrodes. In a further embodiment the processor is configured to determine the presence of amplified nucleic acid in the droplet in substantially real time based on the comparison between electrical impedances of the droplet with corresponding reference electrical impedances. In an embodiment the surfactant includes nanoparticles.

In an embodiment a method of determining a composition of molecules in a droplet includes providing a set of detection electrodes in contact with a fluidic channel, concentrating an analyte at an interfacial boundary of a droplet, flowing the droplet in vicinity of the set of detection electrodes through the fluidic channel, applying an alternating current (AC) power at a first frequency across the set of detection electrodes, obtaining a first measurement value reflecting electrical impedance of the droplet at the first frequency, comparing the first measurement value reflecting electrical impedance of the droplet with a first corresponding reference value, wherein the first corresponding reference value is obtained by measuring a reference droplet containing a known analyte amount in suspension within the reference droplet at the first frequency, and determining presence of analyte in suspension within the droplet based on the comparing.

In an embodiment the set of detection electrodes includes two groups of electrodes, wherein the two groups share a common excitation or detection electrode, and wherein obtaining the first measurement value further includes a differential impedance measurement conducted across the two groups of detection electrodes respectively. In a further embodiment the method includes performing at least three additional differential impedance measurements on the droplet at three additional frequencies conducted across the set of detection electrodes, comparing peak-to-peak voltage values obtained from the three additional measurements with three corresponding reference values respectively, wherein the three corresponding reference values are obtained by measuring the reference droplet at the three additional frequencies respectively, and determining presence of analyte in suspension within the droplet by incorporating results from the three additional measurements. In a further embodiment determining the presence of analyte in the droplet is performed at substantially the same time as obtaining the first measurement value and the performing three additional differential impedance measurements. In an embodiment the concentrating includes bonding a cationic surfactant to the droplet.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION

Embodiments of the present disclosure provide a method and system for concentrating or aligning molecules at a droplet-bulk solution interface, as a means of enhancing a detection sensitivity of the molecules. A number of differing types of intermolecular forces and chemicals or materials can be employed to accomplish the concentrating (and/or aligning). For example, a measurement analogous to a conventional EIS measurement can be made by bringing an analyte (e.g., a molecule to be detected) to the edge of a droplet, and in so doing, positioning the analyte close to an electrode surface to aid in detection. As a non-limiting example, systems and methods according to the present disclosure enable detection of the presence of a gene in genomic DNA (which cannot be detected using whole cells), and further provide a platform that can detect an analyte (e.g., DNA) in flowing droplets. Furthermore, embodiments of the present disclosure include the use of nanoparticles for enhancing a sensitivity of detection for molecules of interest. The use of nanoparticles provides a generalized approach for concentrating analytes at a droplet-bulk solution interface. For example, detection of antigens or antibodies within a droplet are enabled by nanoparticles inducing alignment at the droplet-oil interface. Thus, the system described herein can be used for detection of proteins in addition to nucleic acids.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, components, and circuits have not been described in detail as not to unnecessarily obscure aspects and features of the subject matter.

Some portions of the detailed description are presented in terms of procedures, steps, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "writing," "including," "storing," "transmitting," "traversing," "associating," "identifying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Label-Free Detection of Analytes in Microfluidic Droplets

Embodiments of the present disclosure provide a label-free approach to analyte measurement in droplets, using electrical impedance directly from droplets in order to, for example, generate a readout of assay results of the droplet. Generally, systems and methods of the present disclosure provide means of increasing concentrations of target analytes at the interface of a droplet, as compared with concentrations mixed within the body of the droplet. The analyte is concentrated at an interface of the droplet/bulk solution, for example, at a region adjacent to the outer surface of the droplet. This increases the sensitivity of various measurement modalities to detect the presence, and amount, of analytes. This is in contrast to approaches including bonding of an analyte directly to an electrical lead, and subsequently performing EIS when the analyte binds to the molecule that is bound to the electrical lead. The present approach includes analytes that are contained by a droplet, and the concentration of the analyte in the droplet is measured by EIS. The signal-to-noise (SNR) of measurements of the analyte in the droplet is increased by concentrating the analyte at the interface (e.g., the surface) of the droplet. Further, in contrast to tethering to an electrode, the droplets can be measured as "flowed past" the electrodes.

The analyte can be concentrated by the use of a surfactant of suitable characteristics. As a non-limiting example, for an analyte that is largely anionic (e.g., DNA) or has anionic functional domains, thoughtful selection or design of a cationic surfactant and oil system causes the analyte to arrange and orient at a droplet-oil interface. The cationic surfactant arranges on droplets with hydrophilic (and positively charged) regions oriented toward the droplet. The accumulation of positively charged molecules at the droplet-oil interface induces subsequent accumulation of negatively charged molecules, within the droplet and at the droplet-oil interface, providing alignment and concentration of these molecules at the droplet-oil interface. These and similar techniques are able to improve the sensitivity of droplet electrical impedance measurements by increasing the concentration of the molecules of interest at the droplet surface, which brings these molecules closer to the measurement electrode than conventional approaches (where analyte is dispersed throughout the volume of droplets).

Figure 1:
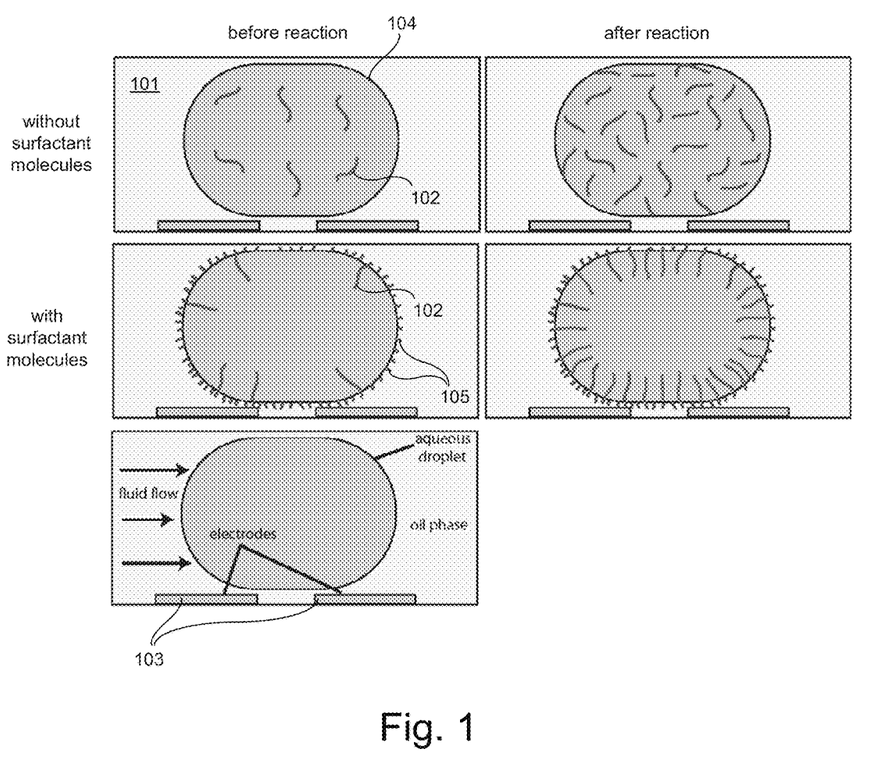
FIG. 1 illustrates a schematic for droplet-based analyte measurement based on the usage of surfactant to concentrate analytes of interest at the droplet-continuous phase interface and an impedance-based detection scheme, according to embodiments of the present disclosure.

Referring now to FIG. 1, a droplet preparation for measurement in a microfluidic apparatus is depicted, according to an embodiment of the present disclosure. According to an embodiment, a droplet 104 is an aqueous droplet, which is immersed in an oil phase bulk solution 101. In operation, droplets 104 within the apparatus are flowed over electrodes 103, which are able to make impedance measurements to perform EIS to characterize analytes 102 that may or may not be contained within droplets of the apparatus. Droplets 104 may be aqueous in nature and surrounded by a continuous phase of oil, or may be lipophilic in nature and surrounded by an immiscible hydrophilic phase. In addition, the droplets may consist of multiple layers (i.e. liposomes or multiple emulsions). For example, a multiple emulsion droplet may consist of an aqueous inner phase, surrounded by a hydrophobic layer or lipid-based membrane, and surrounded by a continuous aqueous or hydrophilic phase (i.e. a W/O/W, or water/oil/water multiple emulsion). Liposomes offer the ability to more closely mimic the functions of a biological cell, and the impedance measurement system described here is envisioned as a way to monitor reactions or processes within these cell analogues.

In an embodiment according to the present disclosure, surfactant molecules 105 are used to attract analytes of interest from the bulk of the droplet to the droplet-continuous phase interface. In these systems, surfactant molecules 105 position themselves at the droplet-continuous phase interface, 104 where analytes 102 to be measured position themselves to associate with the surfactant molecules. This association may be induced at the interface between a droplet 104 and the bulk solution 101, in order to amplify the EIS measurement signal in droplets 104 flowing past electrodes 103. In one embodiment, a CTAB-sodium oleate system is used to induce alignment of nucleic acid molecules to the droplet-oil interface nanoparticles, rather than being evenly dispersed within the bulk of the droplet, as would be the case in absence of the appropriate surfactant. By conjugating molecules of interest to nanoparticles, a CTAB-sodium oleate system may be used to induce collection of nanoparticles at the droplet-oil interface and aid in detection of the analyte.

Such a system brings the analytes of interest from within the bulk of the droplet to the droplet interface, bringing the nanoparticles adjacent to the electrode during measurement, thereby improving SNR. This application may mimic techniques to enhance and amplify EIS measurements through the binding of nanoparticles, conjugated to the target molecules, to the electrode interface. According to embodiments of the present disclosure, EIS (and alternative analyte measurement modalities) can be enhanced by the use of molecular affinity forces (including, but not limited to, intermolecular attractions due to surfactants and covalent bonding induced by complementary protein binding) to align molecules within droplets at the droplet-bulk solution interface. Mechanisms to bring molecules to the droplet-bulk solution interface include dipole or induced-dipole attractions, ion-dipole interactions, ionic attractions, and covalent bonding. These techniques are capable of increasing the sensitivity of electrical impedance measurements in microfluidic droplets, lowering the limit of detection for these systems and enabling detection of droplet contents in a continuously-flowing train of droplets.

As a non-limiting example, detection of single- or double-stranded nucleic acids (which are negatively charged) is enabled through the use of a cationic surfactant, for example hexadecyltrimethylammonium bromide (CTAB). CTAB has traditionally been used for extraction and purification of nucleic acids in solution, due to its ability to bind to the highly negatively-charged nucleic acid molecules. The CTAB molecules align at the droplet-bulk solution interface. The accumulation of positively-charged molecules at the droplet surface induces corresponding accumulation of the negatively-charged nucleic acids at the droplet surface, forming a semi-bilayer of surfactant and nucleic acid molecules. While nucleic acids as analytes are contemplated herein, one can envision positioning antibodies, or proteins, at the edge of the droplet by using a particular surfactant, or combination of surfactants, that is selected to attract the analyte of interest to the surface of the droplet as well.

According to embodiments of the present disclosure, analytes that include proteins can be separated by pH gradients, as proteins equilibrate at a particular pH value (isoelectric point). For example, pH can be used to balance the bulk phase solution, or one can use charge to balance the solution. Further, one can use binding agents, for example interfacial linkages out of the lipid or surfactant. In general, at least three modalities of detection are contemplated: electrical; electro-chemical; and specific binding (e.g., antigen/antibody).

Regarding orientation, electrodes 103 can be arranged such that two (2) or three (3) electrodes are coplanar, all at a bottom of a microfluidic device. Another arrangement is where electrodes are facing, one (or more) at a bottom surface, and one (or more) at a top surface. The use of three electrodes enables cancellation of background noise, and temporal drift. However, detection can be accomplished with only two electrodes. Preferably, if measuring over long timespans, three electrodes are employed in order to account for drift in the signal. Further, sensitivity of systems can be increased as well with three electrodes.

Figure 2:
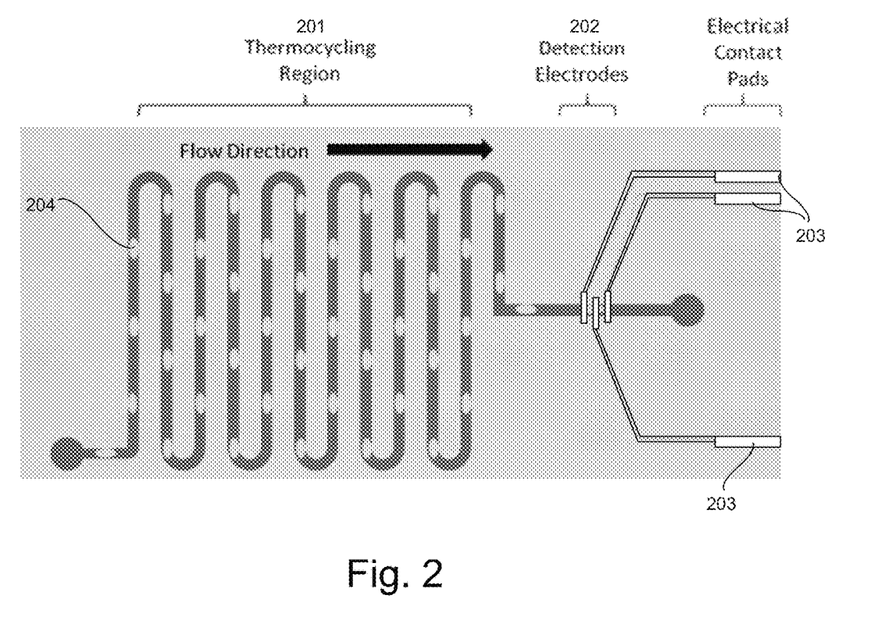
FIG. 2 illustrates an impedance-based detection scheme integrated into an exemplary droplet-based analysis platform, according to embodiments of the present disclosure.

Referring now to FIG. 2, a microfluidic device incorporating an impedance-based detection scheme is depicted. The microfluidic device includes one or more channels forming a reaction region 201 (e.g., a thermocycling region, in the case of PCR), detection electrodes 202, and electrical contact pads 203. Test droplets 204 originating from the reaction region 201 flow over the detection electrodes 202 through a fluidic channel 204, in sequence. Heaters can be optionally integrated with the microfluidic device, such as by being placed underneath the microfluidic device surface, to rapidly heat and cool the reaction region of the microfluidic device. In operation, droplets in solution flow through the reaction region and over the detection electrodes. The detection electrodes can be coupled with a current amplifier and an impedance spectroscope, which provide a measurement mechanism for electrical impedance of each droplet in the fluidic channel 204. In some embodiments, the measurement data can be input to a computing device equipped with suitable hardware and software programs substantially in real-time and are processed in a manner compatible with an embodiment of the present disclosure. In some embodiments, the platform is made part of an automated system and thereby made suitable for performing label-free analyte detection, at high efficiency. The microfluidic device is able to measure the impedance of the solution and detect the presence of an analyte (e.g., molecule of interest) within droplets of the solution, by the integrated detection electrodes. This measurement is label-free, that is, no fluorophore or other type of label is present or necessary for the measurement.

Droplets can be generated in certain size range, and narrower frequency range can be selected to highlight (amplify) only membrane interfacial characteristics for those generated droplet sizes. Droplets are generally approximately 50 microns in diameter, +/−20 microns. However, other droplet sizes are contemplated, such as in a range of 5-500 microns. According to embodiments of the present disclosure, electrode sizes are scaled according to the size of droplets generated for analyte measurement.

Figure 3:
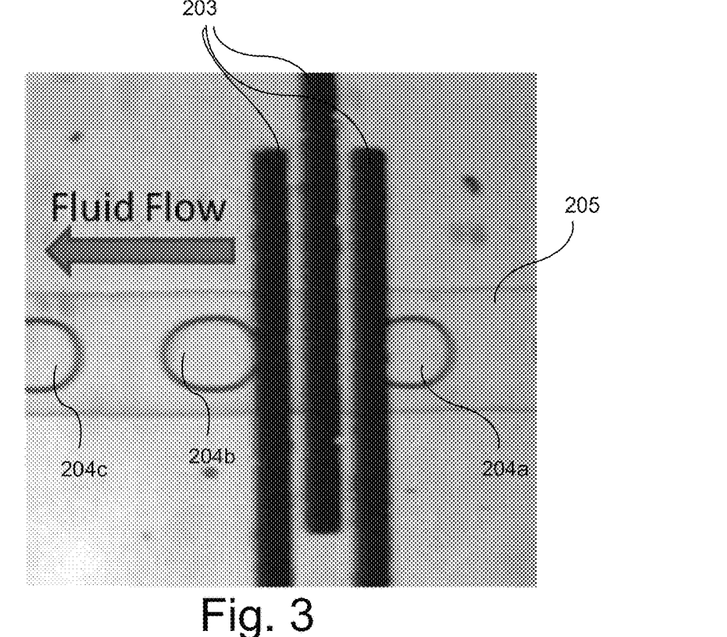
FIG. 3 illustrates a partial schematic configuration of a microfluidic device implementing impedance spectroscopy on droplets to detect an analyte in the droplets, in accordance with an embodiment of the present disclosure.

Differential impedance measurements across the first two electrodes and second two electrodes may be performed using a multi-frequency interrogation scheme and subsequent demodulation. Referring now to FIG. 3, a schematic configuration of a microfluidic device 200 implementing impedance measurement on droplets to detect presence of an analyte (e.g., amplified DNA) in the droplets in accordance with an embodiment of the present disclosure is illustrated. The microfluidic device 200 comprises a microfluidic channel 205 and a set of detection electrodes 203 that are connected to a high frequency or radio frequency power supply for imposing an electrical field on the droplets 204A-204C flowing by. The detection electrodes 203 are spaced and disposed perpendicular to the fluid flow direction in this embodiment. The electrodes may be arranged in either a coplanar or parallel configuration (see figure) for these types of measurements. In this embodiment, the set of electrodes 203 consists of 3 gold electrodes. However, the electrodes could be comprised of any sufficiently conducting material. Examples include other types of thin metal films (such as Cr, Pt or ITO), non-metal conducting surfaces such as carbon black, and thin films with surface area enhanced by roughening. Additionally, multiple sets of electrodes could be used to measure a droplet or set of droplets over time. For example, this could be used to monitor the progress of a nucleic acid amplification or another reaction.

In some embodiments, the test droplet may be measured while it is moving past the detection electrodes. In some other embodiments, the measurement may be performed when the test droplet remains stationary. In some embodiments, differential impedance measurements are employed to determine the electrical impedance of each test droplet, in which an electrical field of a certain frequency is applied to a first two electrodes and then to a second two electrodes. In some embodiments, a common electrode may be shared in the two measurements. The measurements, including excitation signal generation, amplification and demodulation, may be achieved by utilizing an impedance spectroscope (not shown) in combination with a current amplifier (not shown), such as model HF2IS and HF2TA manufactured by Zurich Instruments.

According to embodiments of the present disclosure, analytes encapsulated by droplets disposed in a fluidic channel are interrogated using a differential impedance measurement. For example, in a system including three electrodes, a first electrode can operate to record a voltage, a second electrode can operate to apply a power (e.g., an AC signal), and a third electrode can operate to record a voltage. The signals from the first electrode and third electrode are differenced to produce a signal such as the signal shown in FIG. 6, containing one downward peak and one upward peak per droplet. As a droplet passes over the electrodes, first a downward peak in voltage measured occurs, and then an upward peak (or vice versa, if electrodes connected with opposite polarity). Subsequently, a measurement can be made of a peak-to-peak voltage. In this manner, signal amplitude is twice what would be obtained by a two electrode system. Thus, systems employing three electrodes with differential impedance measurements can be more sensitive (and also have a decreased measurement error). The voltage is proportional to the concentration of the analytes in the droplet. Peak occurs when droplet is spanning only one (1) recording and one (1) voltage-application electrode (e.g., first electrode and second electrode, or second electrode and third electrode).

According to an embodiment, electrodes are approximately 50 microns in width, with a 25 micron gap between adjacent electrodes. Electrodes can be comprised of thin-film gold (e.g., approximately 1000 angstrom in thickness). Alternatively, electrode composition can include platinum, chrome, or other types of metal. According to embodiments, the dimensions of the electrodes are selected according to droplet size generated to encapsulate analytes in the fluidic channels. Generally, a gap between adjacent electrodes is proportional to a minimum droplet size.

Figure 4:
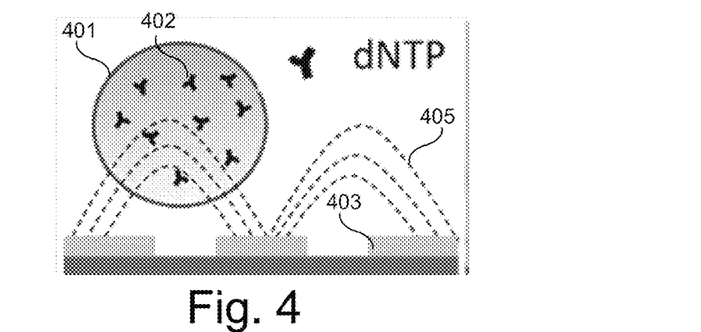
FIG. 4 illustrates a droplet containing unpolymerized DNA monomers flowing over the detection electrodes in accordance with an embodiment of the present disclosure
Figure 5:
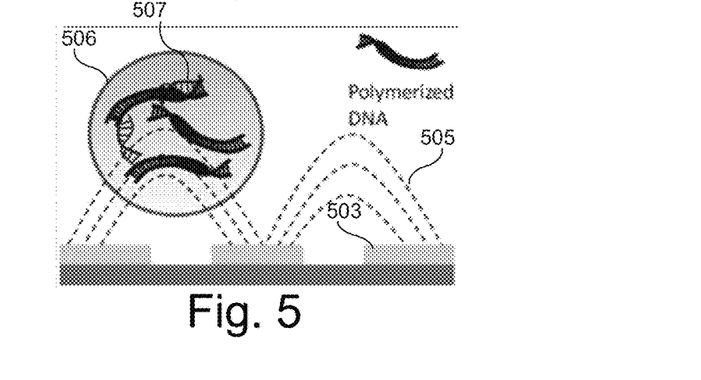
FIG. 5 illustrates a droplet containing polymerized DNA monomers flowing over the detection electrodes in accordance with an embodiment of the present disclosure.

FIG. 4 illustrates a schematic view of a droplet 401 containing non-polymerized DNA monomers 402 flowing over the detection electrodes 403, in accordance with an embodiment of the present disclosure. The dotted lines 405 illustrate electrical field equipotential lines. Also illustrated therein is an exploded view of a single droplet 401 containing non-polymerized DNA monomers 402. Referring now to FIG. 5, a droplet containing polymerized DNA monomers 507 flowing over the detection electrodes 503 in accordance with an embodiment of the present disclosure is illustrated. An exploded view of a single droplet 506 containing polymerized DNA monomers 507 is illustrated as well, with dotted lines 505 illustrating electrical field equipotential lines.

Figure 6:
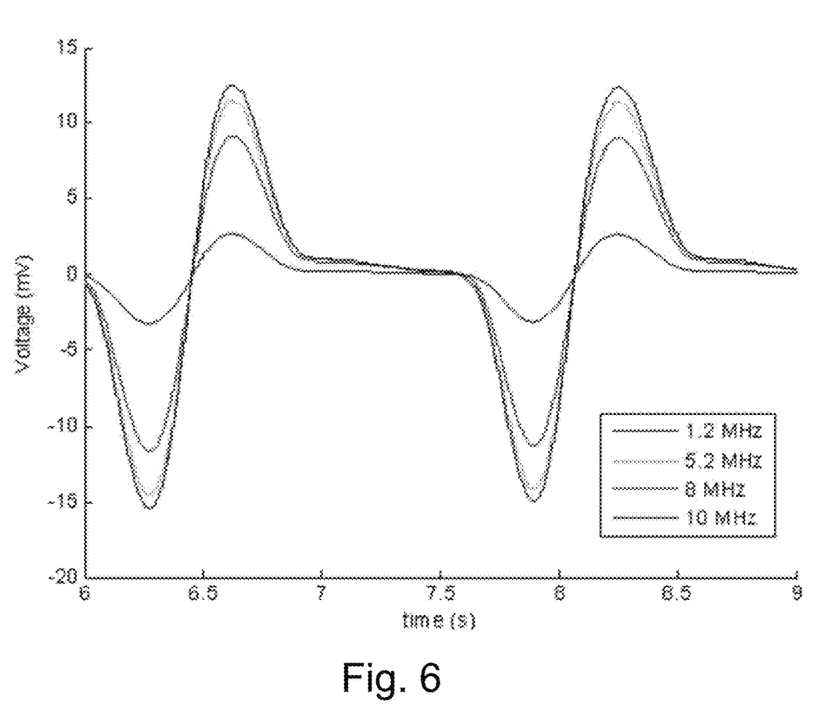
FIG. 6 illustrates peak-to-peak voltage obtained for droplets, recording four separate frequencies simultaneously, according to an embodiment of the present disclosure.

Referring now to FIG. 6, exemplary results obtained from measurements of two droplets are depicted. When performing an impedance measurement at a certain excitation frequency on an individual droplet, the impedance spectroscope can produce a real time voltage-time plot. The amplitude of peak-to-peak voltage extracted from the real time plots is indicative of an electrical impedance of the droplet. The peak-to-peak voltage obtained on the test droplet can then be compared with reference electrical impedance value. In some embodiments, the reference electrical impedance values are peak-to-peak voltages obtained from measuring reference droplets known to contain amplified DNA or non-amplified DNA, respectively, in a similar measuring context with the test droplet measurement, such as the size of the droplets, the frequency applied to the detection electrodes and the conditions of microfluidic channel. In some embodiments, the reference impedance value for a droplet containing non-amplified DNA is obtained by measuring a reference droplet that has not been subject to a PCR procedure. Thus, the presence of amplified DNA on the test droplet is determined based on the comparison. The dependency of the amplitude of the peak-to-peak voltage or impedance signal on droplet size and velocity may be removed by taking into account the residence time of the droplet over the measurement electrodes. Using the residence time to normalize these measurements allows for assessment of the contents of the droplets using their electrical impedance measurements, regardless of variations in size or speed that may occur during testing and measurement operations.

In some embodiments, a multiple-frequency interrogation scheme and subsequent demodulation can be performed on a single test droplet to determine the presence of amplified DNA (or another analyte), for enhanced accuracy. FIG. 6 is sample voltage-time plot obtained from four-frequency measurement on two consecutive droplets, in accordance with an embodiment of the present disclosure. The four excitation frequencies are 1.2 MHz, 5.2 MHz, 8 MHz and 10 MHz, respectively, in this exemplary embodiment. In some other embodiments, the frequencies can be within the range of 10 KHz to 50 MHz.

Figure 7:
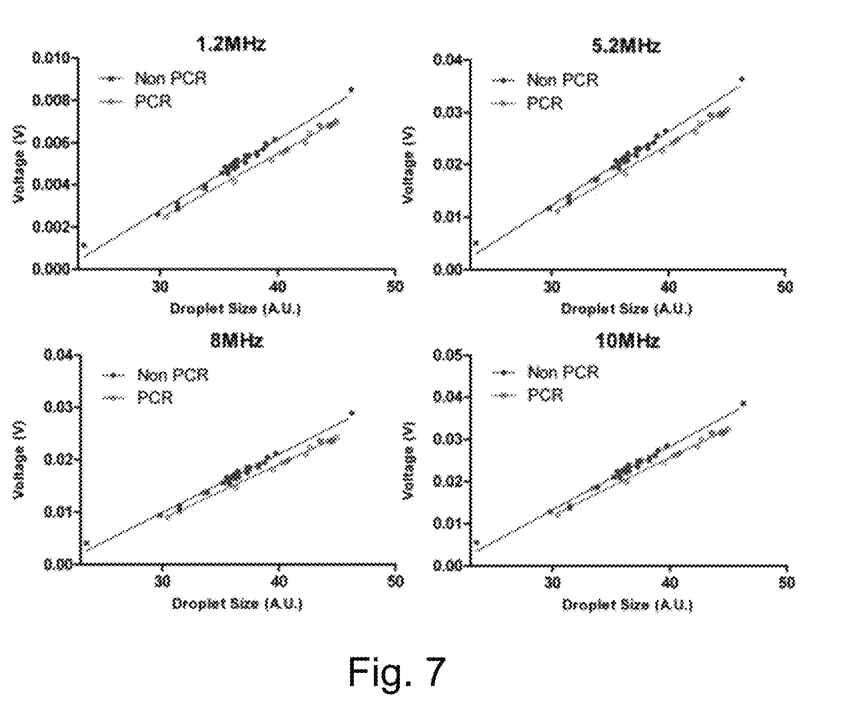
FIG. 7 illustrates sample reference plots of peak-to-peak voltages obtained from measuring reference droplets of a variety of sizes at four frequencies in accordance with an embodiment of the present disclosure.

A reference set of droplets may be used to create standard curves correlating droplet sizes with the measured voltages. As can be seen from FIG. 7, significant differences may exist between the thermocycled and non-thermocycled data sets. In one embodiment, the system and method of the present disclosure may be used as a detection tool, by using the obtained linear fits as reference curves. A separate set of thermocycled and non-thermocycled droplets may be flowed over the electrodes and their size and voltage measurements recorded. The size data may be input into the reference curves and an expected voltage obtained for both thermocycled and non-thermocycled curves. These values may be compared to the measured voltages and the magnitude of the difference between the measured and calculated values was used as the predictor. Using the reference curves in FIG. 7 as a predictor for amplification in a separate set of droplets, a high prediction accuracy is able to be achieved. Combining data from multiple frequencies provides enhanced discriminatory power in detecting droplets containing either unpolymerized nucleotides or polymerized DNA.

In some embodiments, analysis of the impedance data may involve using the magnitude of the electrical impedance. In some other embodiments, the analysis uses only certain features of the impedance, i.e., real or imaginary portions of the impedance measurement, or combination of these.

The result of this is reported in Table 1, which lists sample detection accuracy results achieved by one frequency interrogation and multiple frequency interrogations, respectively, in accordance with embodiments of the present disclosure. Table 1 shows that combining measurement results obtained from multiple frequencies provides enhanced discriminatory power in detecting droplets containing either amplified or non-amplified DNA in the droplets.

TABLE 1

| | % correct, DNA amplified | % correct, DNA not amplified |
|---|---|---|
| Frequency 1 | 94.7 | 100 |
| Frequency 2 | 94.7 | 100 |
| Frequency 3 | 94.7 | 100 |

TABLE 1-continued

| | % correct, DNA amplified | % correct, DNA not amplified |
|---|---|---|
| Frequency 4 | 94.7 | 100 |
| Freq 1 + Freq 2 + Freq 4 | 100 | 100 |

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

Embodiments of the present invention are thus described. While the present invention has been described in particular embodiments, it should be appreciated that the present invention should not be construed as limited by such embodiments, but rather construed according to the following claims.

What is claimed is:

1. A system for increasing sensitivity of detecting a presence of an analyte in a droplet, the system comprising:
  a) a microfluidic device comprising a fluidic channel comprising the droplet, and a set of detection electrodes in contact with the fluidic channel, wherein the set of electrodes measures an electrical impedance of the droplet and detects a presence of an analyte in the droplet, and wherein the fluidic channel forms a reaction region;
  b) a semi-bilayer disposed at an interfacial boundary of the droplet, wherein the semi-bilayer surrounds the droplet, wherein the semi-bilayer comprises i) a surfactant disposed at the interfacial boundary of the droplet, and ii) the analyte positioned at the interfacial boundary and within the droplet, wherein the surfactant associates with the analyte by attracting the analyte from a bulk of the droplet to the interfacial boundary, and wherein the attraction increases a concentration of the analyte at the interfacial boundary of the droplet; and
  c) a power supply, wherein the power supply applies electrical power across the set of detection electrodes at a plurality of known frequencies.

2. The system according to claim 1, wherein the reaction region comprises a thermocycling region for implementing PCR on said droplet.

3. The system according to claim 1, wherein the analyte comprises one of amplified nucleic acid, non-amplified nucleic acid, and protein.

4. The system according to claim 1, wherein the surfactant is covalently bonded to the analyte so as to position the analyte within the droplet at the interfacial boundary.

5. The system according to claim 1, wherein the surfactant is selected to have a charge that is opposite of a charge of the analyte to attract the analyte from the bulk of the droplet to the interfacial boundary of the droplet.

6. The system according to claim 1, wherein the set of detection electrodes measure the electrical impedance of the droplet when the droplet is in motion or stationary relative to the set of detection electrodes.

7. The system according to claim 1, wherein the analyte is bound to nanoparticles.

* * * * *